(12) United States Patent
Lee et al.

(10) Patent No.: US 8,197,728 B2
(45) Date of Patent: Jun. 12, 2012

(54) MOLDED ARTICLES WITH ANTIMICROBIAL PROPERTY AND MANUFACTURING METHOD THEREOF

(75) Inventors: Sung-Hwan Lee, Changwon-si (KR); Sung-Hwa Lee, Changwon-si (KR); Ok-Chun Hyun, Busan (KR); Hyung-Ho Park, Daejeon (KR)

(73) Assignee: LG Electronics, Inc., Seoul (KR)

( * ) Notice: Subject to any disclaimer, the term of this patent is extended or adjusted under 35 U.S.C. 154(b) by 946 days.

(21) Appl. No.: 12/084,560

(22) PCT Filed: Nov. 15, 2006

(86) PCT No.: PCT/KR2006/004815
§ 371 (c)(1),
(2), (4) Date: May 6, 2008

(87) PCT Pub. No.: WO2007/058475
PCT Pub. Date: May 24, 2007

(65) Prior Publication Data
US 2009/0133583 A1    May 28, 2009

(30) Foreign Application Priority Data

Nov. 15, 2005 (KR) .................. 10-2005-0109348
Nov. 15, 2005 (KR) .................. 10-2005-0109349
Nov. 16, 2005 (KR) .................. 10-2005-0109683

(51) Int. Cl.
*A61J 3/07* (2006.01)
*B29C 39/10* (2006.01)
(52) U.S. Cl. .. 264/4; 264/109; 264/176.1; 264/DIG. 48; 264/330
(58) Field of Classification Search ............... 96/226; 210/201; 422/4, 28, 59, 120, 121; 424/93.4, 424/93.45; 427/203, 421.1, 427.4, 430.1
See application file for complete search history.

(56) References Cited

U.S. PATENT DOCUMENTS 2,813,059 A * 11/1957 Davis et al. .................. 424/618
(Continued)

FOREIGN PATENT DOCUMENTS

CN    101085366    12/2007
(Continued)

OTHER PUBLICATIONS

Mauriello G, et al: "Development of Polythene films for Food Packaging Activated with an Antilisterial Bacteriocin from *Lactobacillus Curvatus* 32Y", Jour. of Applied Microbiology, Oxford, GB, vol. 97, No. 2, (2004), pp. 314-322, XP002435150, ISSN: 1364-5072.
Vermeiren I. et al.: "Evaluation of Meat Born Lactic Acid Bacteria As Protective Cultures for the Biopreservation of Cooked Meat Products", Int'l Jour. of Food Microbiology, Elsevier Science Pub., Amsterdam, NL., vol. 96, No. 2, (2004), pp. 149-164, XP00457738,ISSN: 0168-1605.

(Continued)

*Primary Examiner* — Duane Smith
*Assistant Examiner* — Sonji Turner
(74) *Attorney, Agent, or Firm* — McKenna Long & Aldridge LLP

(57) ABSTRACT

The present invention discloses a molded article with an antimicrobial property, and a manufacturing method thereof. The molded article can prevent contact of bacteria or viruses by combining the Kimchi lactic acid bacteria culture fluid having antibacterial and antivirus effects with a raw material. The molded article needing the antimicrobial effect is provided with the antimicrobial property, by incorporating the Kimchi lactic acid bacteria culture fluid with a wide antibacterial spectrum singly or in combination with nano metal particles. The Kimchi lactic acid bacteria culture fluid is combined in the molding step of the article, for reducing the manufacturing time and simplifying the manufacturing process.

11 Claims, 2 Drawing Sheets

A molded article

↑ Combined with a raw material

Kimchi lactic acid bacteria culture fluid

U.S. PATENT DOCUMENTS

| | | | |
|---|---|---|---|
| 2,880,129 A * | 3/1959 | Billings | 427/430.1 |
| 5,458,906 A * | 10/1995 | Liang | 427/2.31 |
| 5,876,489 A * | 3/1999 | Kunisaki et al. | 96/226 |
| 6,762,339 B1 * | 7/2004 | Klun et al. | 602/58 |
| 2004/0121077 A1 * | 6/2004 | Park et al. | 427/383.1 |
| 2004/0241216 A1 * | 12/2004 | Klun et al. | 424/445 |
| 2005/0238631 A1 | 10/2005 | Burwell | |
| 2006/0219641 A1 * | 10/2006 | Kepner et al. | 210/723 |
| 2009/0133583 A1 | 5/2009 | Lee et al. | |

FOREIGN PATENT DOCUMENTS

| | | |
|---|---|---|
| CN | 101085414 | 12/2007 |
| EP | 1 118 342 A1 | 7/2001 |
| EP | 1 475 432 | 11/2004 |
| EP | 1475432 A1 | 11/2004 |
| FR | 2855181 * | 11/2004 |
| JP | 2000-038500 | 2/2000 |
| KR | 2002-0091498 | 12/2002 |
| KR | 2004000623 * | 1/2004 |
| KR | 10-2005-0087741 | 8/2005 |
| KR | 10-2005-0094654 | 9/2005 |
| WO | WO 92/16118 | 10/1992 |
| WO | WO 00/10582 | 3/2000 |
| WO | WO 02/28446 A1 | 4/2002 |
| WO | WO 2006/009394 | 1/2006 |
| WO | WO 2006/009394 A1 | 1/2006 |
| WO | WO 2006/009395 A1 | 1/2006 |
| WO | WO 2007/058476 A2 | 5/2007 |

OTHER PUBLICATIONS

Database WPI, Sec. Ch., Week 200335, Thomson Scientific, London, GB; AN 2003-368966, XP002500228 & KR 2002 091 498 A (Pulmuwon Co. LTD) (2002)—Abstract.

Database WPI, Sec. Ch., Week 200026, Thomson Scientific, London, GB; AN 2000-295744, XP002500229 & JP 2000 038500 A (Sekisui Chem Ind. Co. Ltd.) (2000)—Abstract.

Mauriello et al., "Development of Polythene films for food packaging activated with an antilisterial bacteriocin from *Lactobacillus curvatus* 32Y", Journal of Applied Microbiology 97, pp. 314-322, 2004.

Vermeiren et al., "Evaluation of meat born lactic acid bacteria as protective cultures for the biopreservation of cooked meat products", International Journal of Food Microbiology 96, pp. 149-164, 2004.

Database WPI Section Ch, Week 200335 Thomson Scientific, AN 2003-368966, XP002500228 & KR 2002 091 498 A, Dec. 6, 2002.

Database WPI Section Ch, Week 200026 Thomson Scientific, AN 2000-295744, XP002500229 & JP 2000 038500 A, Feb. 8, 2000.

Cha et al., "Release of nisin from various heat-pressed and cast films", Swiss Society of Food Science and Technology 36, pp. 209-213, 2003.

Park et al., "Identification and Characteristics of Nisin Z-Producing *Lactococcus lactis* subsp. *lactis* Isolated from Kimchi", Current Microbiology, vol. 46, pp. 385-388, 2003.

\* cited by examiner

MOLDED ARTICLES WITH ANTIMICROBIAL PROPERTY AND MANUFACTURING METHOD THEREOF

This application claims the benefit of Korean Patent Application No. 10-2005-0109348, filed on Nov. 15, 2005; Korean Patent Application No. 10-2005-0109349, filed on Nov. 15, 2005; Korean Patent Application No. 10-2005-0109683, filed on Nov. 16, 2005 and PCT Application No. PCT/KR2006/004815, filed on Nov. 15, 2006, which is hereby incorporated by reference for all purposes as if fully set forth herein.

TECHNICAL FIELD

The present invention relates to a molded article with an antimicrobial property and a manufacturing method thereof.

BACKGROUND ART

Recently, with the increasing interest in the hygiene and cleanliness, a number of products have been developed to improve the hygiene and cleanliness. The electronic product field is not an exception. In detail, electric home appliances needing the hygiene and cleanliness include a refrigerator, washing machine, drying machine, air conditioner, air freshener, fan, cleaner, electric pot, electric cooker, dishwashing machine, dish drying machine, microwave oven, mixer, VTR, television, home theater, etc.

Bacteria or fungi which can be parasitic on the surfaces of the products or the components thereof cause diseases such as atopic dermatitis, respiratory trouble, etc., disfigure the products, generate a bad smell, and discolor the external appearances of the products. It is therefore necessary to manufacture an antimicrobial article for protecting the users from the diseases and maintaining the external appearances of the products, by preventing the contact and proliferation of various bacteria and fungi.

Generally, most of antibacterial agents for manufacturing an antibacterial article are chemically synthesized, and the antibacterial agents are expensive and cause harmful side effects. Recently, researches have been actively made on a natural antibacterial material which has an excellent antibacterial property and no side effects harmful for a human body.

Kimchi lactic acid bacteria are generated in fermentation and mature of Kimchi. Safety of the Kimchi lactic acid bacteria as the natural source has been verified by the long time use. It is easy to acquire the Kimchi lactic acid bacteria at a low cost. In addition, the Kimchi lactic acid bacteria have been known as a natural antibacterial material with an excellent antibacterial property and a wide antibacterial spectrum. Moreover, there has been reported that the Kimchi lactic acid bacteria culture fluid could inhibit activities of avian influenza viruses and other similar viruses.

Accordingly, the present inventors have accomplished this invention by molding the article with the antimicrobial property, and using the antibacterial and antivirus effects of the Kimchi lactic acid bacteria culture fluid.

DISCLOSURE OF THE INVENTION

An object of the present invention is to provide a molded article with an antimicrobial property which contains the Kimchi lactic acid bacteria culture fluid with antibacterial and antivirus effects.

Another object of the present invention is to provide a manufacturing method of a molded article with an antimicrobial property which can mold the article by combining the Kimchi lactic acid bacteria culture fluid having antibacterial and antivirus effects with a raw material.

In order to achieve the above-described objects of the invention, there is provided a molded article with an antimicrobial property which contains the Kimchi lactic acid bacteria culture fluid or both the Kimchi lactic acid bacteria culture fluid and nano metal particles.

There is also provided a manufacturing method of a molded article with an antimicrobial property, including a step for molding a wanted shape of article by combining the Kimchi lactic acid bacteria culture fluid or both the Kimchi lactic acid bacteria culture fluid and nano metal particles with a raw material.

BRIEF DESCRIPTION OF THE DRAWINGS

For a better understanding of the invention, reference may be made to the following description of exemplary embodiments taken in conjunction with the accompanying drawings, in which.

BEST MODE FOR CARRYING OUT THE INVENTION

A molded article with an antimicrobial property and a manufacturing method thereof in accordance with preferred embodiments of the present invention will now be described in detail.

Figure 1:
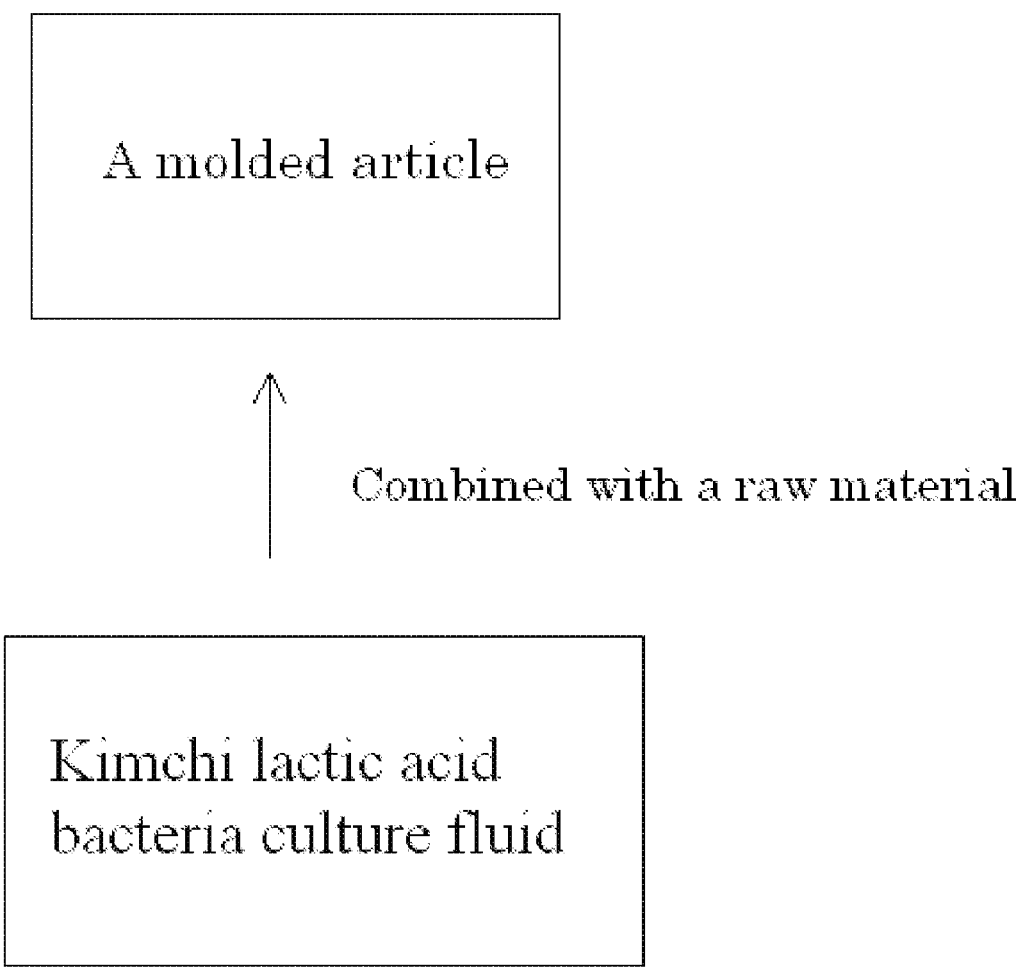
FIG. 1 is a diagram of a molded article comprising Kimchi lactic acid bacteria culture fluid.
Figure 2:
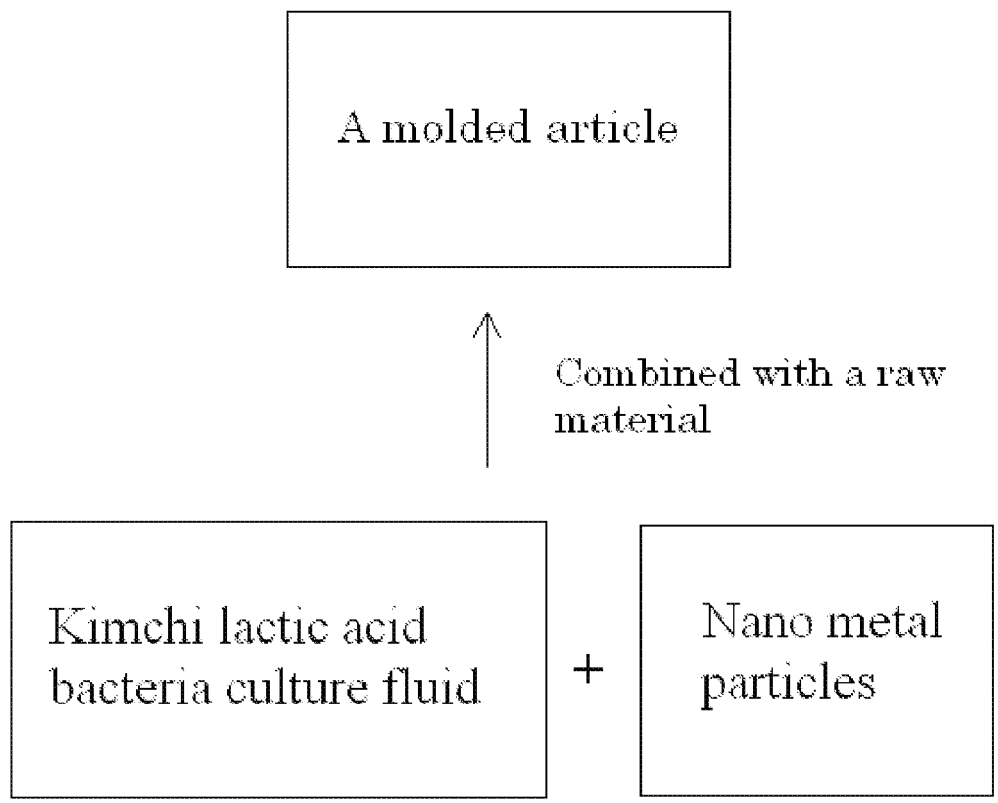
FIG. 2 is a diagram of a molded article comprising both Kimchi lactic acid bacteria culture fluid and nano metal particles.

The present invention provides the molded article with the antimicrobial property which contains the Kimchi lactic acid bacteria culture fluid or both the Kimchi lactic acid bacteria culture fluid and nano metal particles. FIG. 1 is a diagram showing an molded article molded by combining Kimchi lactic acid bacteria culture fluid and a raw material. FIG. 2 is a diagram showing a molded article molded by combining both Kimchi lactic acid bacteria culture fluid and nano metal particles.

Here, the antimicrobial property includes an antibacterial property, an antifungal property and an antivirus property.

The article means all kinds of articles, which bacteria, viruses, etc. may contact to proliferate themselves, without special restriction in use of the article. Therefore, the molded article can be conveniently manufactured by a molding method publicly known in this field, for example, injection molding, extrusion molding, blow molding and thermal molding.

In accordance with one aspect of the present invention, the article can be one of electric home appliances. The electric home appliances mean the whole electric home appliances or the internal or external parts thereof. Exemplary electric home appliances include refrigerator, washing machine, drying machine, air conditioner, air freshener, fan, cleaner, electric pot, electric cooker, dishwashing machine, dish drying machine, water purifier, microwave oven, mixer, VTR, television and home theater. The parts of the electric home appliances are varied according to the kinds of the electric home appliances. For example, the parts of the washing machine are an inner tub, an outer tub, a detergent box, a drum lift, a water supply/drain passage, a filter, etc., the parts of the refrigerator are an inner/outer wall, a cool air duct, a ventilation fan, a door handle, a vegetable box, an ice maker, a filter, etc., and the parts of the air conditioner are an electric heat exchanger, a ventilation fan, an air passage, a filter, etc.

In accordance with another aspect of the present invention, the article can be a filter. Any article performing the filtering function can be used without special restrictions in use, kind and type. Exemplary articles include an air filter, a water filter and a cleaner filter. Any kinds of materials having the filtering function can be used as a material of the filter without special restrictions in kind, type, size and manufacturing process. Exemplary materials include a glass fibers, an ion exchange fiber, a cellulose fiber and an asbestos fiber, various organic and inorganic fibers, a metal such as zinc, copper and aluminum, and a plastic. Such materials can be variously used depending on their characteristics. The type of the filter can be appropriately modified depending on an apparatus the filter used without special restrictions, such as honeycomb type, grain type, net type, filter paper type, cotton type, mesh type, plate type and foam type. In accordance with the present invention, the filter can be used singly or in combination with the existing filter in the same product. Preferably, the article can be an air filter.

In accordance with the present invention, the article can be molded by combining the Kimchi lactic acid bacteria culture fluid or both the Kimchi lactic acid bacteria culture fluid and the nano metal particles with a raw material. Any kinds of raw materials which can form the shape of the article, preferably, the whole electric home appliance or the parts thereof can be used without special restrictions. For example, thermoplastic resin, thermosetting resin, rubber and metal can be used as the raw materials. The raw materials can be used in various ways according to their characteristics. Exemplary raw materials include polymers such as silicone, polyurethane, polyethylene, polypropylene (PP), polyvinylchloride (PVC), latex, acrylonitrile butadiene styrene (ABS), polytetrafluoroethylene (PTFE), polycarbonate (PC) and polyvinylalcohol (PVA). The raw materials can be singly or mixedly used.

In accordance with the present invention, the Kimchi lactic acid bacteria culture fluids acquired through various routes can be used without special restrictions, so far as they have the antibacterial and antivirus effects. For example, the Kimchi lactic acid bacteria culture fluid can be directly extracted from Kimchi, extracted from the cultivated Kimchi lactic acid bacteria, or purchased in a market. Any publicly-known method can be used to cultivate and extract the Kimchi lactic acid bacteria without special restrictions.

In addition, any phases of Kimchi lactic acid bacteria culture fluids can be used without special restrictions, so far as they have the antibacterial and antivirus effects. For example, the Kimchi lactic acid bacteria culture fluid can be selected from the group consisting of the Kimchi lactic acid bacteria culture fluid itself, a concentrate of the Kimchi lactic acid bacteria culture fluid, a dry matter of the Kimchi lactic acid bacteria culture fluid, and mixtures thereof. Any publicly-known method can be used to concentrate and dry the Kimchi lactic acid bacteria culture fluid without special restrictions.

Preferably, the Kimchi lactic acid bacteria are selected from the group consisting of *Leuconostoc* sp. Kimchi lactic acid bacteria, *Lactobacillus* sp. Kimchi lactic acid bacteria, *Weissella* sp. Kimchi lactic acid bacteria, and mixtures thereof. Preferably, the *Leuconostoc* sp. Kimchi lactic acid bacteria are selected from the group consisting of *Leuconostoc citreum, Leuconostoc lactis, Leuconostoc mesenteroides* subsp. *dextranicum, Leuconostoc mesenteroides* subsp. *mesenteroides, Leuconostoc argentinum, Leuconostoc carnosum, Leuconostoc gellidum, Leuconostoc kimchii, Leuconostoc inhae, Leuconostoc gasicomitatum*, and mixtures thereof. More preferably, the *Leuconostoc* sp. Kimchi lactic acid bacteria are selected from the group consisting of *Leuconostoc citreum, Leuconostoc kimchii, Leuconostoc mesenteroides*, and mixtures thereof.

Preferably, the *Lactobacillus* sp. Kimchi lactic acid bacteria are selected from the group consisting of *Lactobacillus brevis, Lactobacillus acidophilus, Lactobacillus bulgaricus, Lactobacillus plantarum, Lactobacillus kimchii, Lactobacillus paraplantarum, Lactobacillus curvatus* subsp. *curvatus, Lactobacillus sakei* subsp. *sakei*, and mixtures thereof.

Preferably, the *Weissella* sp. Kimchi lactic acid bacteria are selected from the group consisting of *Weissella koreensi, Weissella hanii, Weissella kimchii, Weissella soli, Weissella confusa*, and mixtures thereof.

In accordance with the present invention, the Kimchi lactic acid bacteria culture fluid or both the Kimchi lactic acid bacteria culture fluid and the nano metal particles are not uniformly distributed but distributed with a different content ratio in the molded article. For this, the article can be manufactured with the portion containing the Kimchi lactic acid bacteria culture fluid or both the Kimchi lactic acid bacteria culture fluid and the nano metal particles, and the portion containing the Kimchi lactic acid bacteria culture fluid or both the Kimchi lactic acid bacteria culture fluid and the nano metal particles in a lower or no content, by additionally performing an appropriate operation publicly known in this field in the molding step. In general, bacteria or viruses may contact to proliferate freely in the portion of the article that directly meets a medium such as the air and water in which bacteria and viruses are floating. Thus, it is such a portion of the article that needs the antimicrobial property. For this, it is necessary to intensively treat the portion of the article requiring the antimicrobial property with the Kimchi lactic acid bacteria culture fluid. As a result, the same amount of Kimchi lactic acid bacteria culture fluid can improve the substantial antimicrobial effect.

In accordance with the present invention, the molded article can be manufactured by encapsulating the Kimchi lactic acid bacteria culture fluid, and combining the encapsulated Kimchi lactic acid bacteria culture fluid with the raw material. The capsule consists of a core material and a wall material. The core material includes an objective material such as an antibacterial agent, a deodorant agent and an aromatic agent, and the wall material includes micro or nano size grains by forming a thin film with synthetic or natural polymers. Any material which can contain the Kimchi lactic acid bacteria culture fluid can be used as the wall material without special restrictions. Exemplary wall materials include melamine, polyurethane, gelatin, acryl, epoxy, starch, alginate, Chitosan, and mixtures thereof. The encapsulation can be performed according to a method generally used in this field without special restrictions. Once the Kimchi lactic acid bacteria culture fluid is encapsulated, the Kimchi lactic acid bacteria culture fluid is not degenerated at a high molding temperature of the article. The wall material of the capsule is dissolved or burst at a predetermined time after the molding, to spread the Kimchi lactic acid bacteria culture fluid on the whole article. As a result, the antimicrobial effect can be more improved.

In accordance with the present invention, any kinds of metal particles having a sterilizing function can be used as the nano metal particles without special restrictions. Exemplary metal particles include Ag, Zn, Cu, Pt, Cd, Pd, Rh and Cr particles. The metal particles can be singly or mixedly used. The nano metal particles mean metal particles made in a nano size. Any kinds of metal particles made in a nano size can be used without special restrictions in manufacturing process. The nano metal particles prevent propagation of microorganisms such as bacteria, fungi, etc, by restricting the reproduction function of the microorganisms, and interrupt the metabolism of the microorganisms by infiltrating into cells and stopping the enzyme function required in respiration, thereby performing sterilization. In the viewpoint of the antibacterial property and harmlessness to the environment and human body, the nano metal particles are preferably Ag, Zn and Cu nano metal particles, more preferably, nano Ag. Especially, the nano Ag can improve the efficiency of the Kimchi lactic acid bacteria culture fluid.

In addition, the present invention provides the manufacturing method of the molded article with the antimicrobial property, including a step for molding the article by combining the Kimchi lactic acid bacteria culture fluid or the Kimchi lactic acid bacteria culture fluid and nano metal particles with the raw material.

The step for molding the article by combining the Kimchi lactic acid bacteria culture fluid or the Kimchi lactic acid bacteria culture fluid and the nano metal particles with the raw material can be carried out according to a method generally used in this field. Any method which can form the shape of the article can be used without special restrictions. Exemplary molding methods include extrusion molding and injection molding. Since the Kimchi lactic acid bacteria culture fluid is combined with the raw material in the molding step of the article, the manufacturing time is reduced and the manufacturing process is simplified.

In accordance with the present invention, in the molded article with the antimicrobial property, the Kimchi lactic acid bacteria culture fluid or the Kimchi lactic acid bacteria culture fluid and the nano metal particles can be distributed with a different content ratio. For example, the molded article with the antimicrobial property can be manufactured by extrusion or injection-molding one layer by combining the Kimchi lactic acid bacteria culture fluid or the Kimchi lactic acid bacteria culture fluid and the nano metal particles with the raw material, extrusion or injection-molding another layer by combining the Kimchi lactic acid bacteria culture fluid or the Kimchi lactic acid bacteria culture fluid and the nano metal particles with the raw material in a lower content, and jointing the molded layers.

In addition, the molded article with the antimicrobial property can be manufactured by extrusion or injection-molding one layer by combining the Kimchi lactic acid bacteria culture fluid or the Kimchi lactic acid bacteria culture fluid and the nano metal particles with the raw material, extrusion or injection-molding another layer by using the raw material without adding the Kimchi lactic acid bacteria culture fluid or the nano metal particles, and jointing the molded layers. To distribute the Kimchi lactic acid bacteria culture fluid in a different content in a single layer instead of jointing layers, the molded article with the antimicrobial property can be manufactured by combining the Kimchi lactic acid bacteria culture fluid or the Kimchi lactic acid bacteria culture fluid and the nano metal particles with the raw material (raw material 1), combining the Kimchi lactic acid bacteria culture fluid or the Kimchi lactic acid bacteria culture fluid and the nano metal particles with the raw material in a lower content (raw material 2), and individually implanting the raw materials 1 and 2 by performing an appropriate operation in the extrusion or injection molding. Generally, bacteria or viruses may contact to proliferate freely in the portion of the article that directly meets a medium such as the air and water in which bacteria and viruses are floating. Thus, it is such a portion of the article that needs the antimicrobial property. For this, it is necessary to intensively treat the portion of the article requiring the antimicrobial property with the Kimchi lactic acid bacteria culture fluid, by diversifying the content of the Kimchi lactic acid bacteria culture fluid, instead of uniformly combining the Kimchi lactic acid bacteria culture fluid with the raw material and evenly distributing the Kimchi lactic acid bacteria culture fluid on the whole article in the molding. As a result, the same amount of Kimchi lactic acid bacteria culture fluid can improve the substantial antimicrobial effect.

When the Kimchi lactic acid bacteria culture fluid is singly combined with the raw material, any combination method which can form the shape of the article can be used without special restrictions. The combination ratio of the Kimchi lactic acid bacteria culture fluid to the raw material is not specially restricted but appropriately adjusted. Preferably, the amount of the Kimchi lactic acid bacteria culture fluid ranges from 5 to 20 wt %, which is not intended to be limiting. If necessary, such a range can be appropriately adjusted.

Alternatively, when the Kimchi lactic acid bacteria culture fluid and the nano metal particles are combined with the raw material, any combination method which can form the shape of the article can be used without special restrictions. The combination ratio thereof is not specially restricted but appropriately adjusted. Preferably, the amount of the Kimchi lactic acid bacteria culture fluid ranges from 5 to 20 wt %, and the content of the nano metal particles ranges from 100 to 2000 ppm to improve the antimicrobial performance, combination characteristic and molding characteristic. However, if necessary, such ranges are appropriately adjustable.

In addition, the Kimchi lactic acid bacteria culture fluid can be encapsulated before the combination with the raw material, and then combined with the raw material. The encapsulation of the Kimchi lactic acid bacteria culture fluid prevents the Kimchi lactic acid bacteria culture fluid from being degenerated at a high temperature in the molding step of the article. Accordingly, the article can be molded at a relatively high temperature. The encapsulation of the Kimchi lactic acid bacteria culture fluid can be performed according to a method generally used in this field without special restrictions. The molding temperature is not specially restricted but appropriately adjusted according to the characteristic of the raw material of the article. In consideration of the degeneration of the Kimchi lactic acid bacteria culture fluid, preferably, the molding temperature ranges from 100 to 180° C. In the case that the Kimchi lactic acid bacteria culture fluid is encapsulated, degeneration possibility due to the temperature is lowered. As a result, the molding temperature can be raised, for example, to 100 to 250° C.

On the other hand, the manufacturing method can include additional processing steps, such as a drying step and a hardening step after combining the Kimchi lactic acid bacteria culture fluid with the raw material and molding the article. When the article is dried, a drying time and a drying temperature can be adjusted according to the shape, kind and size of the article. If necessary, the molded article can be post-processed into a wanted shape and appropriately used.

Application Examples

In accordance with the present invention, the molded article can be used for various applications. The electric home appliances needing the antimicrobial property are refrigerator, washing machine, air conditioner, cleaner, air freshener, water purifier, humidifier, dishwashing machine, microwave oven, VTR, computer, television, etc.

1) Application to Refrigerator

The parts of the refrigerator such as an inner wall, a cool air duct, a ventilation fan, a door handle, a vegetable box, an air filter, an ice maker and a basket can be molded by combining the Kimchi lactic acid bacteria culture fluid with the raw material.

2) Application to Washing Machine

The parts of the washing machine such as an inner tub, an outer tub, a pulsator, a detergent box, a drum lift and a tub can be molded by combining the Kimchi lactic acid bacteria culture fluid with the raw material. In addition, the present invention can be applied to filters (air filter and water filter) in a dry passage, a water supply/drain passage, and a circulation passage.

3) Application to Air Conditioner

The present invention can be applied to fins of a heat exchanger, an electric heat exchanger (ventilation element), a ventilation fan (metal and molded matter), an air passage (suction unit, discharge unit, louvers, grill, etc.), and an air filter of an indoor unit.

4) Application to Air Freshener

A special Kimchi lactic acid bacteria culture fluid filter can be mounted as one of multiple filters of the air freshener.

5) Application to Dishwashing Machine

The present invention can be applied to a tub, a sump, a screen, a spray arm, a water filter, etc.

Although the preferred embodiments of the present invention have been described, it is understood that the present invention should not be limited to these preferred embodiments but various changes and modifications can be made by one skilled in the art within the spirit and scope of the present invention as hereinafter claimed.

INDUSTRIAL APPLICABILITY

As discussed earlier, in accordance with the present invention, the molded article needing the antimicrobial effect is provided with the antimicrobial property, by incorporating the Kimchi lactic acid bacteria culture fluid with the wide antibacterial spectrum singly or in combination with the nano metal particles. The molded article is also provided with the antivirus property to avian influenza viruses, and similar viruses. The Kimchi lactic acid bacteria culture fluid is combined with the raw material in the molding step of the article, thereby reducing the manufacturing time and simplifying the manufacturing process. Furthermore, in the case that the Kimchi lactic acid bacteria culture fluid is encapsulated, the Kimchi lactic acid bacteria culture fluid is not degenerated at a high molding temperature.

The invention claimed is:

1. A manufacturing method of a molded article with an antimicrobial property, the molded article comprising Kimchi lactic acid bacteria culture fluid originated from Kimchi lactic acid bacteria or both the Kimchi lactic acid bacteria culture fluid and nano metal particles, comprising
a step for encapsulating the Kimchi lactic acid bacteria culture fluid and molding the article by combining the encapsulating Kimchi lactic acid bacteria culture fluid or both the encapsulating Kimchi lactic acid bacteria culture fluid and nano metal particles with a raw material,
wherein the molding step is carried out at a temperature ranging from 100 to 250° C.

2. The manufacturing method of claim 1, wherein the Kimchi lactic acid bacteria culture fluid is selected from the group consisting of the Kimchi lactic acid bacteria culture fluid itself, a concentrate of the Kimchi lactic acid bacteria culture fluid, a dry matter of the Kimchi lactic acid bacteria culture fluid, and mixtures thereof.

3. The manufacturing method of claim 1, wherein the Kimchi lactic acid bacteria are selected from the group consisting of *Leuconostoc* sp. Kimchi lactic acid bacteria, *Lactobacillus* sp. Kimchi lactic acid bacteria, *Weissella* sp. Kimchi lactic acid bacteria, and mixtures thereof.

4. The manufacturing method of claim 3, wherein the *Leuconostoc* sp. Kimchi lactic acid bacteria are selected from the group consisting of *Leuconostoc citreum, Leuconostoc lactis, Leuconostoc mesenteroides* subsp. *dextranicum, Leuconostoc mesenteroides* subsp. *mesenteroides, Leuconostoc argentinum, Leuconostoc carnosum, Leuconostoc gellidum, Leuconostoc kimchii, Leuconostoc inhae, Leuconostoc gasicomitatum*, and mixtures thereof.

5. The manufacturing method of claim 3, wherein the *Lactobacillus* sp. Kimchi lactic acid bacteria are selected from the group consisting of *Lactobacillus brevis, Lactobacillus acidophilus, Lactobacillus bulgaricus, Lactobacillus plantarum, Lactobacillus kimchii, Lactobacillus paraplantarum, Lactobacillus curvatus* subsp. *curvatus, Lactobacillus sakei* subsp. *sakei*, and mixtures thereof.

6. The manufacturing method of claim 3, wherein the *Weissella* sp. Kimchi lactic acid bacteria are selected from the group consisting of *Weissella koreensi, Weissella hanii, Weissella kimchii, Weissella soli, Weissella confusa*, and mixtures thereof.

7. The manufacturing method of claim 1, wherein the molded article is one of the whole electric home appliances or the internal or external parts of the electric home appliances, such as a refrigerator, washing machine, drying machine, air conditioner, air freshener, fan, cleaner, electric pot, electric cooker, dishwashing machine, dish drying machine, water purifier, microwave oven, mixer, VTR, television and home theater.

8. The manufacturing method of claim 1, wherein the molded article is a filter.

9. The manufacturing method of claim 1, wherein the molding step comprises an extrusion or injection molding step.

10. The manufacturing method of claim 1, wherein the raw material is selected from the group consisting of silicone, polyurethane, polyethylene, polypropylene (PP), polyvinylchloride (PVC), latex, acrylonitrile butadiene styrene (ABS), polytetrafluoroethylene (PTFE), polycarbonate (PC), polyvinylalcohol (PVA), and mixtures thereof.

11. A manufacturing method of a molded article with an antimicrobial property, the molded article comprising Kimchi lactic acid bacteria culture fluid originated from Kimchi lactic acid bacteria or both the Kimchi lactic acid bacteria culture fluid and nano metal particles, comprising
a step for molding the article by combining the Kimchi lactic acid bacteria culture fluid or both the Kimchi lactic acid bacteria culture fluid and nano metal particles, with a raw material,
wherein the amount of the Kimchi lactic acid bacteria culture fluid for the combination ranges from 5 to 20 wt %, and the content of the nano metal particles ranges from 100 to 2000 ppm.

* * * * *